(12) United States Patent
Wang et al.

(10) Patent No.: US 9,936,698 B2
(45) Date of Patent: Apr. 10, 2018

(54) MIXED HERBICIDE CONTAINING AMINOPYRALID AND CLOMAZONE

(71) Applicant: NANJING HUAZHOU PHARMACEUTICAL CO., LTD., Nanjing, Jiangsu Province (CN)

(72) Inventors: Jianbing Wang, Nanjing (CN); Yongqiang Peng, Nanjing (CN); Huajun Gan, Nanjing (CN)

(73) Assignee: NANJING HUAZHOU PHARMACEUTICAL CO., LTD., Nanjing (CN)

(*) Notice: Subject to any disclaimer, the term of this patent is extended or adjusted under 35 U.S.C. 154(b) by 131 days.

(21) Appl. No.: 15/100,635

(22) PCT Filed: Apr. 28, 2014

(86) PCT No.: PCT/CN2014/076344
§ 371 (c)(1),
(2) Date: Jun. 1, 2016

(87) PCT Pub. No.: WO2015/081656
PCT Pub. Date: Nov. 6, 2015

(65) Prior Publication Data
US 2017/0208807 A1     Jul. 27, 2017

(30) Foreign Application Priority Data
Dec. 6, 2013   (CN) .......................... 2013 1 0654323

(51) Int. Cl.
*A01N 43/40* (2006.01)
*A01N 43/36* (2006.01)
*A01N 43/80* (2006.01)

(52) U.S. Cl.
CPC ............. *A01N 43/40* (2013.01); *A01N 43/80* (2013.01)

(58) Field of Classification Search
None
See application file for complete search history.

(56) References Cited

FOREIGN PATENT DOCUMENTS

| CN | 102711469 A | 10/2012 |
| CN | 102060799 B | 11/2013 |
| CN | 101808520 B | 6/2014 |
| CN | 103098803 B | 5/2016 |

OTHER PUBLICATIONS

Hu, Zongyan et al., "Aminopyralid, A Novel Herbicide" Pesticides, vol. 45, No. 12, Dec. 25, 2006 (Dec. 25, 2006), pp. 847-848.
International Search Report dated Jul. 4, 2014, Prepared by Endai Kang of ISA/CN for International Application No. PCT/CN2014/076344.
Written Opinion of the ISA dated Jul. 4, 2014, for International Application No. PCT/CN2014/076344.

*Primary Examiner* — Alton N Pryor
(74) *Attorney, Agent, or Firm* — Flener IP & Business Law; Zareefa B. Flener

(57) ABSTRACT

The present invention discloses a mixed herbicide containing aminopyralid and clomazone, which belongs to the technical field of pesticides. The main active ingredients in the herbicide are aminopyralid and clomazone, and the weight ratio of aminopyralid to clomazone is 0.1-80:0.1-80. The present mixed herbicide is useful in weed control in non-arable land, orchards, woodland, corn fields, and rapeseed fields, and has the advantages of quick action, broad herbicidal spectrum, long-lasting effect, thorough weed eradication, low residue, low toxicity, safety, and environmental friendliness, thus being a good chemical herbicide for non-arable land, orchards, woodland, corn fields, and rapeseed fields.

14 Claims, No Drawings

MIXED HERBICIDE CONTAINING AMINOPYRALID AND CLOMAZONE

BACKGROUND

Technical Field

The present invention belongs to the technical field of pesticides and particularly herbicides, and relates to a binary compound formulation of aminopyralid and clomazone. The herbicide composition is useful in weed control in non-arable land, orchards, woodland, maize fields, and rape fields.

Related Art

Aminopyralid has a chemical name of 4-amino-3,6-dichloropyridine-2-carboxylic acid, and is a pyridine herbicide, which is widely used in weed control in upland, grassland, lawns, plantations and non-arable land, and is applicable to controlling annual or perennial broad leaved weeds.

Clomazone is an oxazole herbicide having a chemical name of 2-(2-chlorobenzyl)-4,4-dimethyl-3-isoxazolone. It is a pigment inhibiting preemergence herbicide developed by FMC Corporation (USA), which inhibits the production of chlorophyll and chlorophyll protecting pigments in plants, to cause the plants to die in a short period. When clomazone is absorbed by soybean, the clomazone having active herbicidal property is converted into a degraded product without herbicidal ability after metabolization, such that soybean is protected against the damage therefrom. Clomazone is mainly used for controlling broad leaved weeds and grassy weed, and is useful in weed control in cotton, cassava, corn, rapeseed, sugarcane and tobacco fields in addition to the soybean fields.

At present, the problem of aminopyralid residue is serious, and the amount and method of using aminopyralid are strictly restricted in many countries and regions. To ensure the herbicidal effect of aminopyralid while the residue is reduced, aminopyralid and clomazone at properly reduced amounts are formulated into a mixture for use, so that the herbicidal spectrum is broadened, the herbicidal effect is obviously improved, and the potential remanent harm to after crops is avoided.

SUMMARY

An object of the present invention is to provide a mixed herbicide containing aminopyralid and clomazone.

Another object of the present invention is to provide use of the herbicide in weed control in non-arable land, orchards, woodland, maize fields, and rape fields.

A mixed herbicide containing aminopyralid and clomazone is provided, where the main active ingredients in the herbicide are aminopyralid and clomazone, and the weight ratio of aminopyralid to clomazone is 0.1-80:0.1-80, preferably 1-60:1-60, and most preferably 1:0.5-4.

In the mixed herbicide, the content of aminopyralid and clomazone in the herbicide is 1-85% and preferably 10-75% by weight.

In the mixed herbicide of the present invention, aminopyralid exists in the form of a water soluble salt, including sodium, potassium, ammonium, isopropylamine, methylamine, dimethylamine, ethanolamine, triethanolamine, and triisopropanolamine salts, etc.

In the binary compound formulation of aminopyralid and clomazone according to the present invention, in addition to the active ingredients aminopyralid and clomazone, a pesticidally acceptable conventional surfactant, thickening agent, solvent, or solid filler, and other adjuvants may be added to formulate any pesticidally acceptable formulations, and preferably emulsifiable concentrates, suspensions, aqueous emulsions, microemulsions, soluble concentrates, wettable powders, and water dispersible granules.

"%" mentioned in the present invention is in each case percentages by weight.

When used in weed control in non-arable land, orchards, woodland, corn fields, and rapeseed fields, and particularly in controlling various broad leaved weeds in non-arable land, orchards, woodland, corn fields, and rapeseed fields, the mixed herbicide containing aminopyralid and clomazone according to the present invention has a remarkable effect.

Compared with the prior art, the present invention has the following beneficial effects.

The mixed herbicide of the present invention has the advantages of quick action, broad herbicidal spectrum, long-lasting effect, thorough weed eradication, low residue, low toxicity, safety, and environmental friendliness, thus being a good chemical herbicide for non-arable land, orchards, woodland, corn fields, and rapeseed fields.

DETAILED DESCRIPTION

Example 1

20% of clomazone, 5% of aminopyralid, 5% of calcium dodecylbenzene sulfonate, 3% of an alkyl phenol polyoxyethylene ether, and solvent oil 150# q.s. to 100% were formulated following a conventional method into a 25% by weight (wt %) emulsifiable concentrate, in which aminopyralid existed in the form of an isopropylamine salt.

Example 2

10% of clomazone, 20% of aminopyralid, 3% of an alkyl phenol polyoxyethylene ether, 2% of castor oil polyoxyethylene ether, 0.1% of xanthan gum, 20% of xylene, 5% of ethylene glycol and water q.s. to 100% were formulated following a conventional method into a 30 wt % aqueous emulsion, in which aminopyralid existed in the form of a sodium salt.

Example 3

15% of clomazone, 10% of aminopyralid, 5% of an alkyl phenol polyoxyethylene ether phosphate, 2% of aluminum magnesium silicate, 2% of white carbon black, 5% of ethylene glycol, and water q.s. to 100% were formulated following a conventional method into a 25 wt % suspension, in which aminopyralid existed in the form of a methylamine salt.

Example 4

25% of clomazone, 50% of aminopyralid, 5% of sodium lignin sulfonate, 2% of a dodecyl sulfate, 5% of ammonium sulfate, and kaolin q.s. to 100% were formulated following a conventional method into 75 wt % water dispersible granules, in which aminopyralid existed in the form of a sodium salt.

Example 5

10% of clomazone, 10% of aminopyralid, 5% of sodium dodecylbenzene sulfonate, 3% of an alkyl phenol polyoxyethylene ether, 5% of ammonium sulfate, and kaolin q.s. to 100% were formulated following a conventional method into a 30 wt % wettable powder, in which aminopyralid existed in the form of a sodium salt.

Example 6

15% of clomazone, 60% of aminopyralid, 5% of NNO (sodium methylenedinaphthalene disulphonate) wetting agent, 3% of ammonium sulfate, 2% of polyvinyl alcohol, and kaolin q.s. to 100% were formulated following a conventional method into 75 wt % water dispersible granules, in which aminopyralid existed in the form of a potassium salt.

Example 7

20% of clomazone, 10% of aminopyralid, 6% of NNO (sodium methylenedinaphthalene disulphonate), 5% of sodium lignin sulfonate, and kaolin q.s. to 100% were formulated following a conventional method into a 30 wt % wettable powder, in which aminopyralid existed in the form of a sodium salt.

Example 8

9% of clomazone, 1% of aminopyralid, 5% of calcium dodecylbenzene sulfonate, 5% of castor oil polyoxyethylene ether, 15% of solvent oil 150#, 5% of cyclohexanone, 5% of ethylene glycol, and water q.s. to 100% were formulated following a conventional method into a 10 wt % microemulsion, in which aminopyralid existed in the form of a triisopropanolamine salt.

Example 9

1% of clomazone, 9% of aminopyralid, 5% of sodium dodecylbenzene sulfonate, 5% of an alkyl glycoside, 15% of isopropanol, 5% of cyclohexanone, 5% of ethylene glycol, and water q.s. to 100% were formulated following a conventional method into a 10 wt % soluble concentrate, in which aminopyralid existed in the form of a sodium salt.

Example 10

1. Indoor Activity Test

The co-toxicity coefficients of the formulations obtained in Examples 1-4 on *Alternanthera philoxeroides* were determined.

Test method: Seeds of *Alternanthera philoxeroides* were quantitatively sowed in 9 cm disposable paper cups, each cup having 10-15 seeds, and cultured in a ray radiation incubator. After *Alternanthera philoxeroides* were grown to have 3-6 leave, the *Alternanthera philoxeroides* was sprayed with a crawler crop sprayer. After treatment, the culture was continued in the incubator. The control effect of each treatment on the weed was observed periodically, and the fresh weight of the treated weed was weighed after 30 days. The toxicity regression curve and the co-toxicity coefficient were calculated according to the method proposed by SUN Peiyu et al in 1960. If the co-toxicity coefficient is greater than 100, it is suggested that the two active agents have a synergistic effect; and if the co-toxicity coefficient is less than 100, it is suggested that the two active agents have an antagonistic effect. The test results are shown in Table 1.

TABLE 1

Results of indoor activity test

| Weed | Agent | Regression line | ED50 (ga.i./mu) | Co-toxicity coefficient |
|---|---|---|---|---|
| *Alternanthera philoxeroides* | 48% clomazone emulsifiable concentrate | y = 1.3734x + 1.6096 | 6.41 | — |
| | 30% aminopyralid aqueous solution | y = 1.6810x + 3.3390 | 9.39 | — |
| | Example 1 | y = 1.9136x + 1.4029 | 6.60 | 211.42 |
| | Example 2 | y = 1.3194x + 2.4340 | 5.76 | 243.84 |
| | Example 3 | y = 1.5759x + 1.7228 | 4.63 | 252.20 |
| | Example 4 | y = 1.6224x + 1.9042 | 8.10 | 203.86 |

It can be seen from Table 1 that the co-toxicity coefficients of the two active agents after compounding are all greater than 100, indicating that the mixed herbicide of the present invention has an obvious synergistic effect.

2. Field Efficacy Test

Test agent: 4 binary compound herbicides obtained in Examples 1-4.

Control: 48% clomazone emulsifiable concentrate (commercially available), and 30% aminopyralid aqueous solution (commercially available).

Crop: corn.

Control target: *Commelina communis, Galium aparine* var. *tenerum, Alternanthera philoxeroides, Capsella bursa-pastoris,* and *Portulaca oleracea* L.

Test method: The agents were accurately weighed according to the area of the test plot, diluted with water, and evenly sprayed using a knapsack sprayer with a fan nozzle dedicated for herbicides. During spray, care should be taken to evenly spray the solution to the test plot, to avoid the occurrence of missed and excessive spray.

After test, the death of weeds was observed respectively on days 20 and 40 after application of the agents, and the herbicidal activities of the agents were compared.

The weed control efficacies of the example formulations of the present invention are shown in Tables 2 (20 days after application) and 3 (40 days after application) below.

TABLE 2

Results of field efficacy test (20 days after application)

| Treatment agent | Dosage (ga.i./mu) | Control effect on *Commelina communis* (%) | Control effect on *Galium aparine* var. *tenerum* (%) | Control effect on *Alternanthera philoxeroides* (%) |
|---|---|---|---|---|
| Example 1 | 15 | 92 | 93 | 92 |
| Example 2 | 15 | 93 | 95 | 94 |
| Example 3 | 15 | 94 | 95 | 95 |
| Example 4 | 15 | 93 | 92 | 93 |
| 30% aminopyralid aqueous solution | 20 | 90 | 88 | 87 |
| 48% clomazone emulsifiable concentrate | 15 | 88 | 86 | 84 |

TABLE 3

Results of field efficacy test (40 days after application)

| Treatment agent | Dosage (ga.i./mu) | Control effect on *Commelina communis* (%) | Control effect on *Galium aparine* var. *tenerum* (%) | Control effect on *Alternanthera philoxeroides* (%) |
|---|---|---|---|---|
| Example 1 | 15 | 85 | 85 | 83 |
| Example 2 | 15 | 86 | 85 | 83 |
| Example 3 | 15 | 88 | 87 | 85 |
| Example 4 | 15 | 85 | 83 | 82 |
| 30% aminopyralid aqueous solution | 20 | 77 | 71 | 76 |
| 48% clomazone emulsifiable concentrate | 15 | 76 | 73 | 71 |

It can be seen from Tables 2 and 3 that the mixed herbicide of the present invention has a remarkable control effect on broad leaved weeds, exhibits an obvious synergistic effect, and has the advantages of quick action, and long-lasting effect.

What is claimed is:

1. A mixed herbicide containing a synergistically effective amount of aminopyralid and clomazone, wherein the main active ingredients in the herbicide are aminopyralid and clomazone, and the weight ratio of aminopyralid to clomazone is 0.1-80:0.1-80.

2. The mixed herbicide containing aminopyralid and clomazone according to claim 1, wherein the weight ratio of aminopyralid to clomazone in the herbicide is 1-60:1-60.

3. The mixed herbicide containing aminopyralid and clomazone according to claim 2, wherein the weight ratio of aminopyralid to clomazone in the herbicide is 1:0.5-4.

4. The mixed herbicide containing aminopyralid and clomazone according to claim 1, wherein percent by weight of aminopyralid and clomazone in the herbicide is 1-85% by weight.

5. The mixed herbicide containing aminopyralid and clomazone according to claim 4, wherein percent by weight of aminopyralid and clomazone in the herbicide is 10-75% by weight.

6. The mixed herbicide containing aminopyralid and clomazone according to claim 1, wherein the aminopyralid exists in the form of a water soluble salt, selected from the group consisting of sodium, potassium, ammonium, isopropylamine, methylamine, dimethylamine, ethanolamine, triethanolamine, and triisopropanolamine salts.

7. The mixed herbicide containing aminopyralid and clomazone according to claim 1, which is formulated into formulations with aminopyralid and clomazone as main active ingredients and with pesticidally acceptable adjuvants.

8. The mixed herbicide containing aminopyralid and clomazone according to claim 7, wherein the formulations selected from the group consisting of emulsifiable concentrates, suspensions, aqueous emulsions, microemulsions, soluble concentrates, wettable powders, and water dispersible granules.

9. A method of weed control comprising applying the mixed herbicide according to claim 1 to weeds in non-arable land, orchards, woodland, corn fields, and rapeseed fields.

10. A method of weed control comprising applying the mixed herbicide according to claim 1 to various broad leaved weeds in non-arable land, orchards, woodland, corn fields, and rapeseed fields.

11. The mixed herbicide containing aminopyralid and clomazone according to claim 2, wherein the aminopyralid exists in the form of a water soluble salt, selected from the group consisting of sodium, potassium, ammonium, isopropylamine, methylamine, dimethylamine, ethanolamine, triethanolamine, and triisopropanolamine salt.

12. The mixed herbicide containing aminopyralid and clomazone according to claim 3, wherein the aminopyralid exists in the form of a water soluble salt, selected from the group consisting of sodium, potassium, ammonium, isopropylamine, methylamine, dimethylamine, ethanolamine, triethanolamine, and triisopropanolamine salts.

13. The mixed herbicide containing aminopyralid and clomazone according to claim 4, wherein the aminopyralid exists in the form of a water soluble salt, selected from the group consisting of sodium, potassium, ammonium, isopropylamine, methylamine, dimethylamine, ethanolamine, triethanolamine, and triisopropanolamine salt.

14. The mixed herbicide containing aminopyralid and clomazone according to claim 5, wherein the aminopyralid exists in the form of a water soluble salt, selected from the group consisting of sodium, potassium, ammonium, isopropylamine, methylamine, dimethylamine, ethanolamine, triethanolamine, and triisopropanolamine salt.

\* \* \* \* \*